US00PP27371P3

(12) United States Plant Patent
Whitcomb

(10) Patent No.: US PP27,371 P3
(45) Date of Patent: Nov. 15, 2016

(54) ***VITEX* PLANT NAMED 'WHIT L'**

(50) Latin Name: *Vitex negundo*
Varietal Denomination: WHIT L

(71) Applicant: Carl E. Whitcomb, Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 14/544,428

(22) Filed: Jan. 27, 2015

(65) Prior Publication Data

US 2016/0219775 P1 Jul. 28, 2016

(51) Int. Cl.
*A01H 5/00* (2006.01)

(52) U.S. Cl.
USPC ..... Plt./226

(58) Field of Classification Search
USPC ..... Plt./216, 226
See application file for complete search history.

*Primary Examiner* — Susan McCormick Ewoldt
*Assistant Examiner* — Karen Redden
(74) *Attorney, Agent, or Firm* — Jeffrey L. Streets

(57) ABSTRACT

A new and distinct variety of *vitex, Vitex negundo*, particularly distinguished by having a compact, much branched, dwarf growth habit, with dense dark green leaves, interspersed with spikes of sterile, blue-purple flowers.

3 Drawing Sheets

Genus, species: *Vitex negundo.*
Varietal denomination: 'WHIT L'.

BACKGROUND OF THE INVENTION

1. Field of the Invention

The present invention relates to a new and distinct variety or cultivar of the ornamental shrub, *Vitex negundo*, commonly known simply as *vitex* or vernacular names such as chaste tree, spice lilac, spice tree, monks pepper-tree, wild pepper, Indian spice, hemp-tree, sage-tree, wild lavender, tree of chastity.

2. Description of the Related Art

*Vitex negundo* is native to a broad area of China and SE Asia and has naturalized over a much wider area of the middle East and Africa. One hypothesis is that Chinese traders preparing to travel the silk road, would pack seeds and leaves of *Vitex* in among goods to prevent damage from insects and rodents. Along the route, seeds of *Vitex* would be inadvertently dispersed. It seems likely that *Vitex agnus-castus*, considered to be native to the middle East and parts of southern Europe and northern Africa, derived from ancestral Chinese *Vitex negundo* seeds centuries ago. It was introduced into cultivation in North America about 1600.

*Vitex* flowers on new growth and produce large quantities of seeds. Seedlings of *Vitex negundo* have become so invasive in some areas so as to be considered a weed. The plant constantly emits a pleasant and distinct spice-like odor during the growing season. Brush a twig or a few leaves and release of the volatile oil increases. The volatile oil acts as a deterrent to most insects, for example, grasshoppers are commonly seen hiding among leaves, yet feeding does not occur. Even when dormant, the odor remain sufficient to prevent rodent damage and deer from feeding on branches or rubbing on large stems.

In the USA, an assortment of seedlings have been selected, given varietal names and introduced into the nursery trade. Criteria for selection have been flower color, size of panicles and other growth features. However, to date, use in landscapes has been limited because all become large plants that produce lots of troublesome seeds. To date, no *vitex* cultivars have been patented.

The new dwarf and sterile variety of *vitex* claimed herein, which has been given the cultivar name 'WHIT L' is a seedling selected from a block of about 8,000 seedlings which were 11 generational descendants from the original parent used to begin this research in 1986. The plant is from this breeding program that began in 1986, in which the parent was selected based on many features that were desirable, but not exceptional. The seeds from the parent are extremely variable, with wide ranging features. The plant 'WHIT L' was the only seedling saved from approximately 450 seedling from the parent.

This new and distinct *vitex* was asexually reproduced by rooting softwood cuttings taken from the original 'WHIT L' plant near Stillwater, Okla. The asexually reproduced plants show all of the unique features that characterize of this *vitex*. As a further test, cuttings were taken from the asexually propagated plants. These secondary cuttings rooted and grew the same as the parent, indicating that the unique features of this plant are stable through successive generations of asexual reproduction.

SUMMARY OF THE INVENTION

The plant of the present invention is a new and distinct variety of *vitex, Vitex negundo* which has been given the cultivar name 'WHIT L' and is characterized by sterile blue-purple flowers, a low growing, much branched dwarf growth habit that may reach a height of 3 to 4 feet with age. The original 'WHIT L' is now four years old and has remained compact and free of disease or insect damage.

Leaves are opposite and palmate with typically 3 to 5 leaflets, densely clustered at the ends of short branches. Leaflets of the plant emerge medium green with a light purple cast near the base that quickly disappears. Mature leaves are uniformly dark green Inflorescences are in panicled spikes between about 4 and 6 inches long and between about 1.0 to 1.5 inches wide. Flower buds are gray. Individual flowers are blue-purple.

Flowers are sterile.

Flowers begin opening at the base of the panicled spikes and progresses upward to the tip. Under Oklahoma conditions, flowering begins in mid-summer and flowers remain attractive for 3 to 4 weeks. Because 'WHIT L' cultivar is sterile, after the first flower flush ages, additional flowering occurs, typically continuing until frost.

DETAILED BOTANICAL DESCRIPTION

Figure 1:
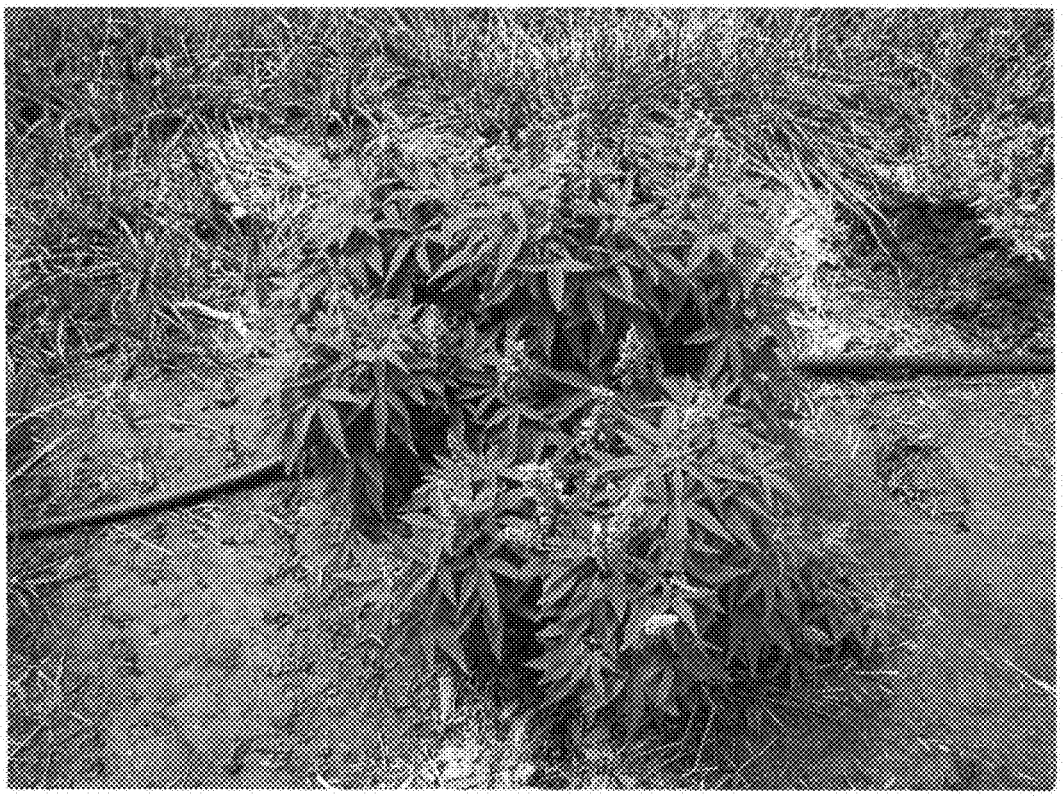
FIG. 1 is a full color photographic view of our new dwarf *vitex* plant 'WHIT L' at an age of four years old showing its growth and flowering habit near Stillwater, Okla.

The following botanical description is of the new and distinct dwarf cultivar of *vitex, Vitex negundo*, which has been given the cultivar name 'WHIT L' at an age of four years old. Specific color designations set forth by number designations are in accordance with The Royal Horticultural Society Colour Chart (1966). General color recitations are consistent with ordinary American color terminology.

The *vitex* cultivar 'WHIT L' has not been observed under all possible environmental conditions. It is to be understood that the phenotype may vary significantly with variations in environment such as soils, temperature, light intensity and length of day without differences in the genotype of the plant. The following botanical characteristics and observations are taken from plants when grown under normal outdoor conditions in north central Oklahoma. Unless otherwise noted, the following descriptions is of plants propagated from the original parent plant growing in a field near Stillwater, Okla., but is also consistent with plants ranging from a few months to 18 months growing in containers in north central Oklahoma.

THE PLANT

Type: Deciduous woody shrub with multiple stems and dense branching.

Classification: *Vitex, Vitex negundo.*

Growth habit: The plant has multiple stems creating a low spreading irregular mound. Individual stems of the first growth flush typically grow 4 to 8 inches then terminate in flower spikes in early to mid summer. As flowers of the first flush age, additional shoots, typically 2 to 4 inches long are produced, terminating in additional flower spikes. The repeat flowering process typically continues for the remainder of the growing season until frost, unless interrupted by severe drought or herbicide injury.

Origin: An open pollinated seedling selected from a block of about 8,000 seedlings which were 11 generational descendants from the original parent used to begin this research in 1986 near Stillwater, Okla.

Propagation: The plant is easy to propagate from softwood cuttings under mist, with the distinguishing characteristics of the asexually propagated offspring remaining identical to the parent.

Size and shape: Growth of *vitex*, 'WHIT L' cultivar in an open field near Stillwater, Okla. is irregular in overall shape, with typically about 10 to 12 inches height growth per year with a spread of about 15 to 20 inches. It is estimated that 'WHIT L' cultivar may reach a height of 3 to 4 feet with a spread of 5 to 6 feet. The stated height and spread of the new dwarf 'WHIT L' cultivar is much smaller than other cultivars. Specifically, the most widely grown *vitex* plant currently grown in the nursery trade is a cultivar called Shoal Creek that grows to a height of 20 feet or more, and has a spread of nearly the same as the height. Accordingly, the 3 to 4 foot height of the new dwarf "WHIT L" cultivar is about $1/5^{th}$ as tall than the most widely grown *vitex* cultivar, and the 5 to 6 foot spread of the new dwarf "WHIT L" cultivar is about $1/3^{rd}$ the spread of the most widely grown *vitex* cultivar.

Hardiness: The new variety of *vitex* has withstood temperature of about 0 degrees F. in the field with no injury.

Pests and disease: *Vitex* is highly resistant to all insects and rodents known to exist in north central Oklahoma. Through 28 years of growing 150,000 or more *vitex* seedlings through 11 generations, damage from deer or rodents or insects or disease has not been observed.

THE FLOWERS

Blooming period: Blooming begins in mid-July in north central Oklahoma and continues until frost. The flowering period is longer than most seedlings and cultivars of *vitex* known to me. Flowering continues during periods of intense and prolonged heat as long as drought does not become severe. Because the plant is sterile, flowers remain showy longer than is typical of the species. As flowers age and begin to fade, new shoots are produced that terminate in additional flower spikes as shown in FIG. 1.

Petals: Flowers are sessile or nearly so, corolla, blue-purplish, (violet, 88-A or B), 3/16 to 3/8 inches long, funnelform, slightly curved, typically 2 lipped, 5 lobed, lobes more or less ovate. The upper surface of the petals is purplish (violet, 88-A or B). In high light, the lower surface of the petals is also purplish (violet, 88-A or B), but with coulds or lower light the lower surface of the petals can range from 53-B or C.

Figure 2:
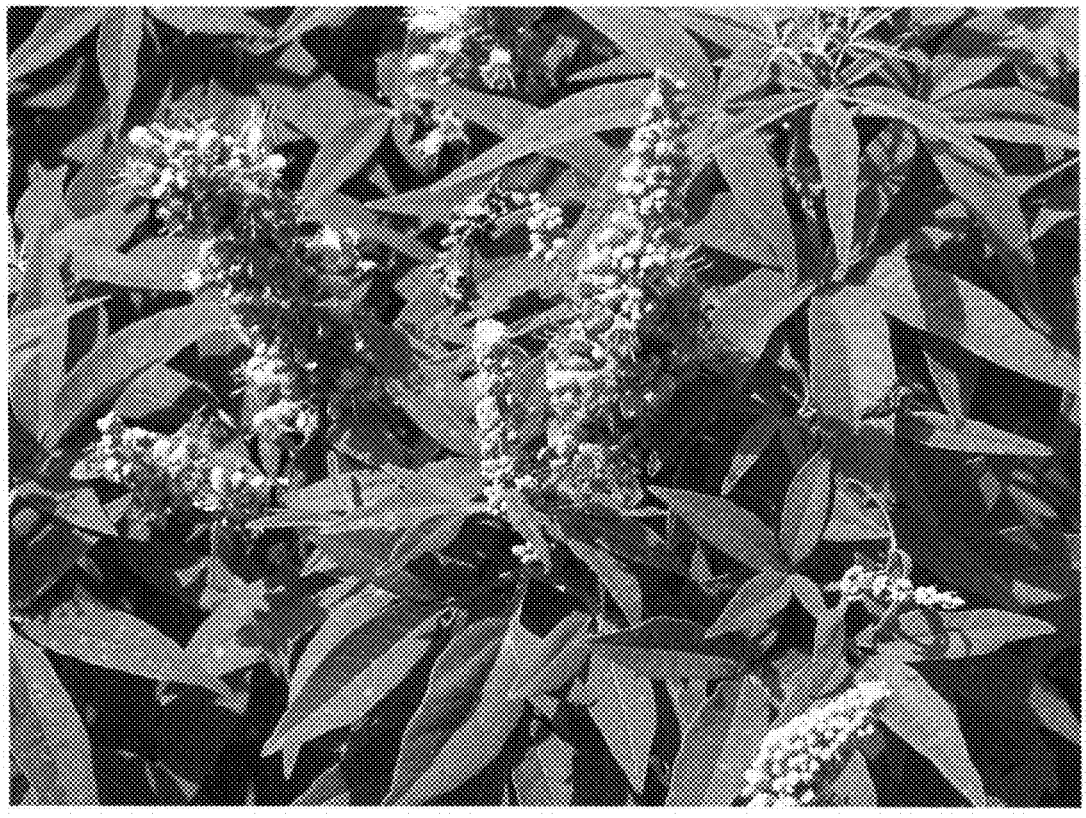
FIG. 2 is a full color photographic view of our new dwarf *vitex* plant 'WHIT L' at an age of four years old showing both unopened and open flowers.

Inflorescences: Inflorescences are panicled spikes. Individual flowers are sessile or with very short pedicel. Flowers first open at base of the panicled spikes and progress upward, FIGS. 1 and 2. Flowers are fragrant, with a spice-like aroma. An inflorescence may contain from about 25 to 200 flowers or more as shown in FIGS. 1 and 2. Once flowers open, flower color remains the same during warm or cool conditions, sun or clouds, until finally shriveling slightly and dropping cleanly to expose the calyx or occasionally turning light brown at first (199-A) and later dark brown (200-A or B) before dropping. Because of the complex and irregular branching of the inflorescence, precise assignments of colors to structural parts is difficult. Inflorescences are between about 4 and 6 inches long and between about 1.0 to 1.5 inches wide.

Stamens: Stamens typically extend beyond the petals with filaments similarly colored like the flowers (88-A or B or C) and anthers variously deformed and ranging from light brown (199-A or B) to near black (201-A).

Sepals: Calyx, campanulate, about ⅛ inch long, densely grayish pubescent (156-A, B or C) ranging to slightly greenish (157-A or B) on the outside, irregularly 5 toothed, teeth more or less triangular. In the absence of flowers and seeds, calyx centers are dark green, (about 147-A).

Buds: Unopened flower buds are globular, ranging from about 1/16 to 3/16 inch diameter, covered with dense white-pubescence (155-A or B) to more grayish ((156-A or B).

Seeds: The plant is sterile. Furthermore, the femail floral parts (pistil, ovary, and stigma) are variously deformed and irregular, and form a tangled mixture of deformed parts down among the petals, which likely accounts for the plant being sterile.

THE FOLIAGE

Figure 3:
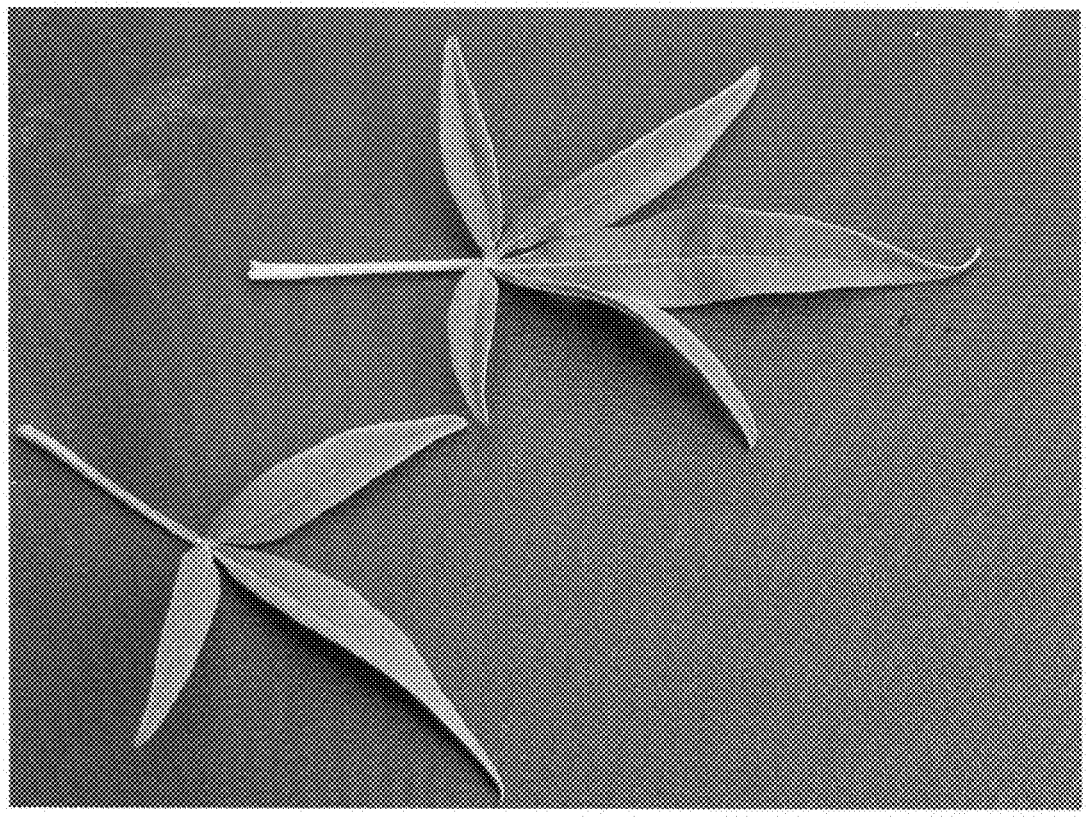
FIG. 3 is a full color photographic view of typical leaves of our new dwarf *vitex* plant 'WHIT L' at an age of four years old showing the compound leaves with both 3 and 5 leaflets.

Leaf shape: Leaves are sessile, opposite, deciduous, palmately compound, typically with 3 or 5 leaflets, but occasionally with 4, 6 or 7 on a very short central petiole. Individual leaves have a central and more prominent leaflet typically subtended by 2 or 4 slightly smaller leaflets. Individual leaflets are long, lanceolate, with a smooth margin, and ranging from 2.5 to 3.5 inches long early in the season as shown in FIG. 3 and 1.0 to 2.25 inches late in the season.

Leaf color: In the spring and summer, both upper and lower surface are lighter green when young (146-A or B), sometimes briefly young leaflet bases are blue-purple (187-A or B), soon maturing to a darker dull green (147-A or B) on both upper and lower surfaces. Leaf petiole may range from green when in full sun (147-B or C) to a slightly purplish-green in shade (no color match found in the R.H.S. colour chart). There is no fall color. With the first frost, leaves turn dark brown (200-C or D) to near black and are retained until dislodged by wind or rain.

Leaf texture: Leaves are smooth on both upper and lower surfaces.

Leaf size: Leaves produced early in the season are typically largest, ranging from 3.5 to 5 inches long overall, from base of petiole to tip of longest leaflet, and 3.0 to 4.0 inches wide. Leaves produced in mid-summer and progressively later in the growing season are smaller, ranging from 1.5 to 2.5 inches long and 1.25 to 2.0 inches wide.

THE BRANCHES AND BARK

Branch color: Young stems are typically grayish-yellow-green (148-A or B), intermediate stems are more yellow-green (152-A or B) and mature stems are brown (199-A or B). Stem colors are transitional with age and plant development and are therefore not precise.

Branch length: First growth branches are typically 4 to 6 inches long, while mid-summer and fall branches are 2 to 4 inches, depending on season and growing conditions.

Branch diameter: Early season branch diameter typically ranges from ¼ to 7/16 inches. Late season branch diameter is typically ⅛ to ¼ inch.

Bark: Smooth on young branches, with broad ridges on mature stems. Bark of mature stems and branches is a medium to dark brown (199-A or B).

I claim:

1. A new and distinct variety of *vitex* plant, substantially as illustrated and described.

* * * * *